(12) United States Patent
Feger et al.

(10) Patent No.: US 7,485,240 B1
(45) Date of Patent: Feb. 3, 2009

(54) ELECTROLYTE FOR HIGH VOLTAGE ELECTROLYTIC CAPACITORS

(75) Inventors: Christopher R. Feger, Clemson, SC (US); Jesse S. Shaffer, Columbia, SC (US)

(73) Assignee: Pacesetter, Inc., Sunnyvale, CA (US)

( * ) Notice: Subject to any disclaimer, the term of this patent is extended or adjusted under 35 U.S.C. 154(b) by 303 days.

(21) Appl. No.: 11/427,632

(22) Filed: Jun. 29, 2006

(51) Int. Cl.
*A61N 1/39* (2006.01)
*H01G 9/00* (2006.01)

(52) U.S. Cl. .................. 252/62.2; 361/503; 361/504; 361/505; 607/5

(58) Field of Classification Search ............... 252/62.2; 429/326, 339, 344; 361/503, 504, 505; 607/5
See application file for complete search history.

(56) References Cited

U.S. PATENT DOCUMENTS

| | | |
|---|---|---|
| 4,518,471 A | 5/1985 | Arora |
| 4,525,249 A | 6/1985 | Arora |
| 4,885,115 A | 12/1989 | Yokoyama et al. |
| 4,975,806 A * | 12/1990 | Clouse ................ 361/505 |
| 5,202,042 A * | 4/1993 | Tsuji et al. ............. 252/62.2 |
| 5,522,851 A | 6/1996 | Fayram |
| 5,715,133 A | 2/1998 | Harrington et al. |
| 6,275,373 B1 | 8/2001 | Marshall et al. |
| 6,404,619 B1 | 6/2002 | Marshall et al. |
| 6,587,329 B1 | 7/2003 | Feger |
| 6,589,441 B1 | 7/2003 | Feger |
| 6,687,117 B2 | 2/2004 | Liu et al. |
| 6,773,632 B1 | 8/2004 | Marshall et al. |
| 2003/0142464 A1 | 7/2003 | Liu et al. |

FOREIGN PATENT DOCUMENTS

EP  1333455 A2  6/2003

* cited by examiner

*Primary Examiner*—C. Melissa Koslow
(74) *Attorney, Agent, or Firm*—Steven M. Mitchell

(57) ABSTRACT

An electrolyte including γ-butyrolactone, a cosolvent and an alcohol is disclosed, which may be used in an electrolytic capacitor with very high operating voltage. Optional additional additives are added to the electrolyte to enhance its conductivity and reliability.

19 Claims, 4 Drawing Sheets

Comparison to Commercially Available Mixed Solvent Electrolyte

ELECTROLYTE FOR HIGH VOLTAGE ELECTROLYTIC CAPACITORS

BACKGROUND OF THE INVENTION

1. Field of the Invention

This invention relates to an electrolyte for an electrolytic capacitor, particularly a high voltage electrolytic capacitor, which requires enhanced reliability.

2. Background Art

Compact, high voltage capacitors are utilized as energy storage reservoirs in many applications, including implantable medical devices. These capacitors are required to have a high energy density since it is desirable to minimize the overall size of the implanted device. This is particularly true of an Implantable Cardioverter Defibrillator (ICD), also referred to as an implantable defibrillator, since the high voltage capacitors used to deliver the defibrillation pulse can occupy as much as one third of the ICD volume.

Implantable Cardioverter Defibrillators typically use two electrolytic capacitors in series to achieve the desired high voltage for shock delivery. For example, an implantable cardioverter defibrillator may utilize two 350 to 400 volt electrolytic capacitors in series to achieve a voltage of 700 to 800 volts.

A strategy for increasing energy density in the capacitor, and thus reducing its size, is to minimize the volume taken up by the paper and cathode foil and maximize the number of anodes. This may be achieved by using a multi-anode stack configuration. A multiple anode stack configuration requires fewer cathodes and paper spacers than a single anode configuration and thus reduces the size of the device. A multiple anode stack consists of a number of units consisting of a cathode, a paper spacer, two or more anodes, a paper spacer and a cathode, with neighboring units sharing the cathode between them. However, to charge and discharge the inner anodes (furthest from the cathode) charge must flow through the outer anodes. With typical anode foil, the path through an anode is quite tortuous and results in a high equivalent series resistance (ESR) for a multi-anode configuration. Thus, ESR increases as more anodes are placed together in the stack. To combat this problem, very low resistivity electrolytes may be used in a multi-anode configuration without an excessive ESR increase.

Another strategy for decreasing the size of the device, is to increase the operating voltage of a single capacitor. If the operating voltage is increased sufficiently, an ICD could be designed with only one electrolytic capacitor. The ability to use a single electrolytic capacitor in an ICD would increase the packaging efficiency, thus reducing the device size. The capacitor, however, would require operating voltages well over 400 Volts. What is needed, therefore, is a capacitor with very high operating voltages and components capable of reliably functioning in a very high voltage electrolytic capacitor.

BRIEF SUMMARY OF THE INVENTION

In one embodiment, the present invention relates to a conductive electrolyte for a very high voltage electrolytic capacitor, including γ-butyrolactone, acetonitrile, and glycerol.

In another embodiment, the present invention relates to a conductive electrolyte for a very high voltage electrolytic capacitor, including an aprotic, polar solvent selected from the group consisting of γ-butyrolactone, N-methylpyrrolidinone and mixtures thereof; a cosolvent selected from the group consisting of acetonitrile, dimethyl sulfoxide (DMSO) and mixtures thereof, and an alcohol selected from the group consisting of glycerol, diethylene glycol monoalkyl ether, 2-alkoxy ethanol and mixtures thereof.

In another embodiment, the present invention relates to a conductive electrolyte for a very high voltage electrolytic capacitor, including γ-butyrolactone, acetonitrile, glycerol, dodecanedioic acid, diisopropylethylamine and 3-nitrobenxyl alcohol.

These and other objects, advantages and features will become readily apparent in view of the following detailed description of the invention.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

The present invention will now be described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE INVENTION

Reference will now be made in detail to the embodiments of the present invention, examples of which are illustrated in the accompanying drawings and examples. Certain embodiments of the present invention will now be described in detail. While specific configurations and arrangements are discussed, it should be understood that this is done for illustrative purposes only. A person skilled in the relevant art will recognize that other configurations and arrangements can be used without departing from the spirit and scope of the invention. It will be apparent to a person skilled in the relevant art that this invention can also be employed in a variety of other devices and applications.

The present invention relates to a highly conductive electrolyte for very high voltage electrolytic capacitors and to an electrolytic capacitor impregnated with the electrolyte of the present invention for use in an implantable cardiodefibrillator (ICD). The electrolytes of the present invention may be used in a multi-anode configuration without an excessive ESR increase.

The electrolytes of the present invention generally include solvents that give the electrolyte its bulk properties of viscosity, boiling point and salvation. The electrolytes optionally further include a conducting ionic species that contributes to the specific conductivity, how aggressive the electrolyte is toward other components in the capacitor and the pH. The electrolytes generally may further comprise other additives such as a depolarizer.

The invention disclosed herein describes an electrolyte that is primarily based on γ-butyrolactone (BLO). BLO provides significant advantages over traditional glycol based electrolytes in that high withstand voltage formulations can be obtained with a reasonable conductivity and low viscosity, resulting in low ESR devices. The formulations are also less sensitive to subtle shifts in local concentrations of components and thus provide a higher reliability device. In a multiple anode stack configuration intended for ICD usage, the low viscosity provides excellent ionic mobility of charge carriers necessary for low ESR.

However, BLO alone as a solvent is insufficient to meet all these requirements and several co-solvents may be employed. One such co-solvent is acetonitrile which provides an additional conductivity boost to the electrolyte due to its high dielectric constant while not changing the viscosity significantly. Another additive such as glycerol may be necessary to ensure complete solubility of larger dicarboxylic acids, as well as to provide —OH groups to serve as an oxygen source during capacitor aging and reformation. A cathode depolarizer such as nitroanisole or nitrobenzyl alcohol may also be employed to reduce the possibility of gas formation during capacitor discharge. Lastly, the choice of base to neutralize the acid is important, as strong bases such as ammonia or dimethylamine can exhibit attack on the BLO, which results in the formation of potentially detrimental byproducts. Therefore, a trisubstituted amine such as trimethylamine, diethylamine, or diisopropylethylamine is used to reduce the possibility of BLO decomposition. Other solvents that could be used include DMSO in place of acetonitrile or any number of glycols and alcohols in place of glycerin. The acid typically is an eight to thirteen carbon chain acid, although longer chain dicarboxylic acids may be employed. The mix order is not particularly vital, provided that all components have been adequately solubilized.

The resultant composition, when combined with an appropriate separator pad, either a manila, esparto, or hemp paper as typical Kraft papers are not sufficiently wetted by predominantly BLO compositions, or a porous polymer spacer such as Celgard, will provide a high reliability, low ESR device at voltages in excess of 500 volts. In proper combination, it is possible to push this composition to very high voltages near or at about 700-750 volts, which would allow for a single capacitor within an ICD, greatly simplifying construction and yields.

In one embodiment, the present invention relates to a conductive electrolyte for a very high voltage electrolytic capacitor, including γ-butyrolactone (BLO), acetonitrile, and an alcohol selected from the group consisting of glycerol, diethylene glycol monoalkyl ether, 2-alkoxy ethanol and mixtures thereof.

Examples of diethylene glycol monoalkyl ethers for use in the present invention include, but are not limited to, diethylene glycol monomethyl ether, diethylene glycol monoethyl ether, diethylene glycol monopropyl ether, diethylene glycol monobutyl ether, diethylene glycol monopentyl ether and diethylene glycol monohexyl ether.

Examples of 2-alkoxy ethanols for use in the present invention include, but are not limited to, 2-methoxy ethanol, 2-ethoxy ethanol, 2-propoxy ethanol, 2-butoxy ethanol, 2-pentoxy ethanol, 2-hexyloxy ethanol, 2-heptyloxy ethanol and 2-octyloxy ethanol.

BLO imparts low viscosity to the electrolyte and increases its corrosion resistance, due, in part, to its hydrophobic nature. Alcohols, such as glycerol (glycerin), increase the conductivity of the electrolyte, increase the solvation of any ionic species, and facilitate the swelling of paper spacers, if used in the capacitor. Acetonitrile is very similar to BLO in that it also increases the conductivity and decreases the viscosity of a resultant electrolyte. The combination of the acetonitrile and the alcohol allow for a wide range of viscosities to be achieved in electrolyte formulation, without adversely impacting the quality and reliability of the electrolytes.

In one example, which is not meant to be limiting, the electrolyte includes about 75 wt % to about 95 wt % γ-butyrolactone, about 1 wt % to about 10 wt % acetonitrile and about 1 wt % to about 10 wt % alcohol. In another example, the electrolyte includes about 80 wt % to about 90 wt % γ-butyrolactone, about 4 wt % to about 6 wt % acetonitrile, and about 4 wt % to about 6 wt % alcohol. In a further example, the electrolyte includes γ-butyrolactone, acetonitrile and glycerol, with about 75 wt % to about 95 wt % γ-butyrolactone. In a still further example the electrolyte includes γ-butyrolactone, acetonitrile and glycerol, with about 1 wt % to about 10 wt % acetonitrile. In yet another example, the electrolyte includes γ-butyrolactone, acetonitrile and glycerol, with about 1 wt % to about 10 wt % glycerol.

Electrolytes of the present invention optionally further comprise an amine. Any amine can be used that is capable of forming an ionic salt with a carboxylic acid and forming a conductive electrolyte for use in a very high volt capacitor. Examples of amines for use in the invention include, but are not limited to, ammonia, methylamine, dimethylamine, trimethylamine, ethylamine, diethylamine, triethylamine, ethanolamine, diethanolamine, triethanolamine, and diisopropylethylamine.

Electrolytes of the present invention optionally further comprise a dicarboxylic acid. Any dicarboxylic acid can be used that is capable of forming a salt with an amine and forming a conductive electrolyte for use in a very high volt capacitor. Examples of dicarboxylic acids include, but are not limited to, aliphatic dicarboxylic acid of carbon chain length from five to fifteen ($C_5$-$C_{15}$). More particular examples, which are not meant to be limiting, include, but are not limited to, adipic acid, 3-tert-butyl adipic acid, suberic acid, azelaic acid, sebacic acid, undecanedioic acid, dodecandioic acid and brassylic acid.

The ionic salt resulting from the combination of the amine and the dicarboxylic acid acts as an ionic conducting species, which contributes to the conductivity of the electrolyte and the pH of the electrolyte. The conductivity is therefore related to the pH of the electrolyte. The ionic salts are non-aggressive towards other components of the capacitor. The combination of dicarboxylic acids having high molecular weight and thermally stable amines results in extremely stable ionic salts. The greater stability of the ionic salts imparts long term reliability to the finished capacitor.

Electrolytes of the present invention can be any pH, as long as the electrolyte has reasonable conductivity at the operating temperature and can be used in electrolytic capacitors having very high working voltages. In one example, the electrolytes of the present invention have pH from about 5.5 to about 9.0. While electrolytes having pH values outside this range would function, the conductivity of the electrolyte may decrease and may affect the overall performance of the electrolyte.

Hydrogen gas is known to evolve from areas of leakage current during normal operation of hermetically sealed, high voltage electrolytic capacitors. If allowed unabated, the pressure would rise to a point of rupture of the containment vessel, thus shortening the operating life and reliability of the capacitor. Electrolytes of the present invention, therefore, optionally further comprise a depolarizer. Depolarizers are well known to those of relevant skill in the art. Any depolarizer may be used that is capable of inhibiting the formation of gases, or binding or removing any gasses that form in the capacitor, and can be formulated in a conductive electrolyte for use in a very high volt capacitor. Examples of depolarizers for use in the present invention include, but are not limited to, nitro-substituted aromatic compounds. Specific examples, which are not meant to be limiting, include but are not limited to, nitrobenzene, nitrotoluene, nitrophenol, nitroacetophenone, nitrobenzyl alcohol and nitroanisole. In examples where more than one substituent is present on the aromatic ring, the nitro group may be present on any other position. The naming of the compound generically, therefore, is meant to include compounds of all possible positional isomers. For example, nitrobenzyl alcohol is used herein to include 2-nitrobenzyl alcohol, 3-nitrobenzyl alcohol and 4-nitrobenzyl alcohol. Depolarizers are optionally formulated in electrolytes from about 0.5 wt % to about 3 wt %.

Electrolytes of the present invention optionally further comprise other additives to enhance the operating performance and/or extend the lifetime and improve the reliability of the capacitor. For example, the electrolytes of the present invention optionally further comprise additives that protect the bare anode during operation of the capacitor. In one example, the additive is hypophosphorous acid.

Electrolytes of the present invention optionally further comprise co-solvents. The cosolvents modify the conductivity, viscosity, solubilizing, maximum breakdown voltage and other properties of the electrolyte. Examples of cosolvents for use in the present invention include, but are not limited to, aprotic, polar solvents. Specific examples include, but are not limited to, N-methylpyrrolidinone (NMP) and dimethyl sulfoxide (DMSO).

In another embodiment, the present invention relates to a conductive electrolyte for a very high voltage electrolytic capacitor, which includes an aprotic, polar solvent that is γ-butyrolactone, N-methyl pyrrolidinone, or mixtures thereof, acetonitrile, and an alcohol selected from the group consisting of glycerol, diethylene glycol monoalkyl ether and 2-alkoxy ethanol. In one example, the electrolyte includes about 45 wt % to about 85 wt % γ-butyrolactone, about 5 wt % to about 45 wt % N-methyl pyrrolidinone, about 1 wt % to about 10 wt % acetonitrile and about 1 wt % to about 10 wt % alcohol.

In another embodiment, the present invention relates to a conductive electrolyte for a very high voltage electrolytic capacitor, which includes γ-butyrolactone, DMSO and an alcohol selected from the group consisting of glycerol, diethylene glycol monoalkyl ether, 2-alkoxy ethanol and mixtures thereof. In one example, the electrolyte includes about 75 wt % to about 95 wt % γ-butyrolactone, about 1 wt % to about 10 wt % DMSO and about 1 wt % to about 10 wt % alcohol.

In another embodiment, the present invention relates to a conductive electrolyte for a very high voltage electrolytic capacitor, which includes γ-butyrolactone, acetonitrile and glycerol. The electrolyte optionally further comprises diisopropylethylamine, dodecanedioic acid, 3-nitrobenzyl alcohol and hypophosphorous acid. In one example, the electrolyte includes about 80 wt % to about 90 wt % γ-butyrolactone, about 4 wt % to about 6 wt % acetonitrile, about 4 wt % to about 6 wt % glycerol, not more than about 10 wt % dodecanedioic acid, not more than about 5.0 wt % diisopropylethylamine, not more than about 3.0 wt % 3-nitrobenzyl alcohol and not more than about 1.0 wt % hypophosphorous acid. A preferred embodiment consists primarily of BLO (about 86 wt %) with acetonitrile and glycerin in concentrations of about 5 wt % each. The balance is made up of the base diisopropylethylamine (about 1.0%), dodecanedioic acid (about 2.5%), and 3-nitrobenzyl alcohol (about 0.5%). The resulting water content is quite low to aid in stability and performance.

The electrolytes of the present invention may be used in electrolytic capacitors having very high operating voltages. In one example, electrolytes of the present invention may be used in electrolytic capacitors having operating voltages greater than about 500 Volts. In another example, electrolytes of the present invention may be used in electrolytic capacitors having operating voltages in the range of about 500-750 Volts.

The electrolytes of the present invention also exhibit good conductivities. In one example, electrolytes of the present invention exhibit a conductivity from about 0.1 to about 5.0 mS/cm at a temperature from about 20 to about 80° C. In another example, electrolytes of the present invention exhibit a conductivity from about 100 to about 1000 μS/cm at a temperature from about 20 to about 80° C.

Figure 1:
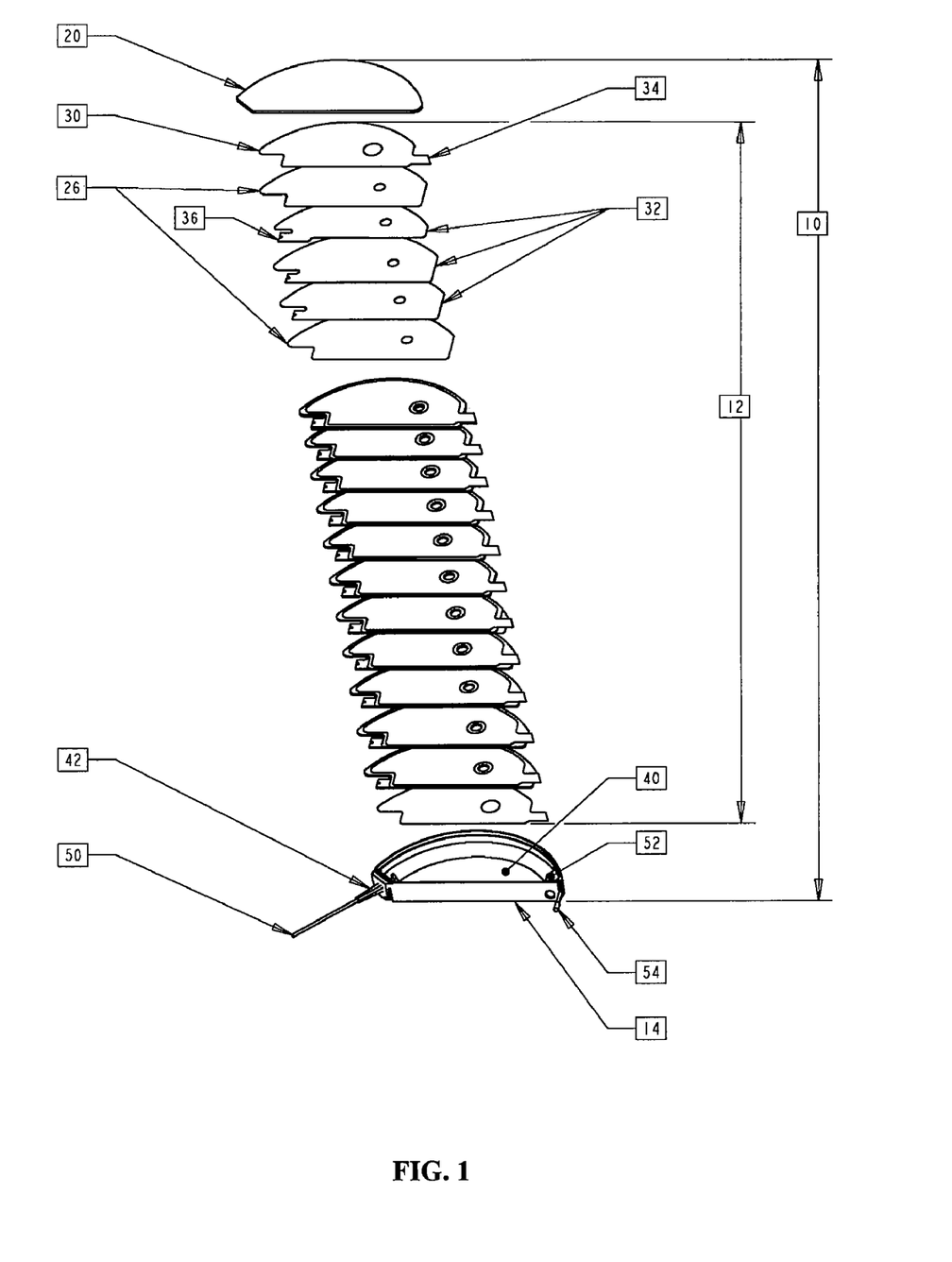
FIG. 1 is a representation of a multiple anode flat, stacked capacitor prepared in accordance with an embodiment of the present invention.

A multi-anode flat capacitor may be manufactured according to the present invention. FIG. 1 illustrates a capacitor 10 having a multiple anode flat, stacked capacitor configuration 12 according to the present invention. Flat stack 12 consists of alternating conductive and separator sheets within a housing 14 enclosed by a lid 20. The sheets alternate between paper separator sheets 26, and conductive cathode sheets 30 or multiple layer anode sheets 32. In the spaces formed between adjacent separator sheets, the cathodes alternate with the multiple layer anodes. In an embodiment, the dielectric is provided by an oxide layer on the etched surface of the anodes, while the cathode includes the conductive sheets, the electrolyte-saturated separator layers, and the electrolyte that fills the tunnels on the surface of the anodes. Each of the cathodes 30 has a cathode tab 34, all of which are registered with each other to be compressed together for electrical interconnection. Similarly, each of the anodes 32 has an anode tab 36, registered with each other to be compressed together for electrical interconnection. The illustration shows each anode layer having three anodes per layer for example, although according to the present invention, there may be two or more anodes per layer. Additionally, one or both of the end cathodes may be removed, with the housing itself connected to the other cathodes and functioning as a cathode. The housing 14 is an aluminum container that defines a chamber 40 in which the stack 12 is closely received. The chamber has a depth equal to the thickness of the stack. The housing is provided with a feed through connector 42, which has an electrically conductive lead 50 that extends out of the housing for connection to other circuitry, with an insulative sleeve surrounding the lead and closely received in a bore defined in the wall of the housing to form an environmental seal. The anode tabs 36 are welded together and electrically connected to the terminal of feed through 42. The housing also includes a cathode attachment step 52 in its interior at a position registered with the ends of the cathode tabs 34, so that the tabs may be staked or welded as a bundle to the step for electrical connection to the housing. A cathode lead 54 is directly electrically connected to the housing for connection to the cathodes. In an embodiment in which the cathode is isolated from the housing, in which the housing is non-conductive, or in which cathodes of different groups are isolated from each other, insulated feed-throughs like those for the anodes may be used.

In one example, aluminum foil is used as the anode and cathode layers. Aluminum foil produces a sufficient quality oxide layer, has good conductive properties, and is widely available. In other examples, other valve metal foils conventionally utilized in electrolytic capacitors may also be used, including, but not limited to, titanium, tantalum, magnesium, niobium, zirconium and zinc. In one example, a strip of unetched, high purity (99.99%) aluminum foil with a cubicity of greater than 85% in the <100> direction is used. Such foils are well-known in the art and are readily available from commercial sources known to those skilled in the art.

The anode foil is etched in an aqueous halide based etch solution, typically a hydrochloric acid or sodium chloride solution, according to a conventional etch process; for example, U.S. Pat. No. 5,715,133 to Harrington et al. describes a suitable method of etching foil and is incorporated herein by reference in its entirety. The etch solution, in one example, includes about 1.3% by weight sodium chloride, 3.5% by weight sodium perchlorate, 0.35% sodium persulfate, and deionized water. The etch solution is heated to a temperature from about 60° C. to about 95° C. In one example, the electrolyte is heated to about 85° C. The foil is etched at a DC current density of about 0.01 A/cm$^2$ to 0.30 A/cm$^2$. In one example, the foil is etched to about 0.15 A/cm$^2$. A charge of 20 to 100 coulombs per cm$^2$ is passed through the foil during the etching process. In one example, about 50 coulombs/cm$^2$ is passed through the foil, which requires a time of about 2 minutes and 13 seconds to 11 minutes and 7 seconds. In a specific example, the charge is passed through the foil for about 5 minutes and 30 seconds.

The foil is then removed from the etch solution and rinsed in deionized water. Then the tunnels formed during the initial etch are widened, or enlarged, in a secondary etch solution, typically an aqueous based nitrate solution. The solution includes about 1% to about 20% aluminum nitrate. In one example, the solution includes about 10 to about 14% aluminum nitrate, with less than about 1% free nitric acid. The etch tunnels are widened to an appropriate diameter by methods known to those in the art, such as that disclosed in U.S. Pat. No. 4,518,471 to Arora and U.S. Pat. No. 4,525,249 to Arora, entirely incorporated herein by reference.

After the etch tunnels have been widened, the foil is again rinsed with deionized water and dried. Finally, a barrier oxide layer may be formed onto one or both surfaces of the metal foil by placing the foil into an electrolyte bath and applying a positive voltage to the metal foil and a negative voltage to the electrolyte. The barrier oxide layer provides a high resistance to current passing between the electrolyte and the metal foils in the finished capacitor, also referred to as the leakage current. A high leakage current can result in the poor performance and reliability of an electrolytic capacitor.

The formation process consists of applying a voltage to the foil through an electrolyte such as boric acid and water or other solutions familiar to those skilled in the art, resulting in the formation of an oxide on the surface of the anode foil. In one example, the electrolyte for formation is a 100-1000 µS/cm, alternatively about 500 µS/cm, citric acid concentration. In the case of an aluminum anode foil, the formation process results in the formation of aluminum oxide ($Al_2O_3$) on the surface of the anode foil. The thickness of the oxide deposited or "formed" on the anode foil is proportional to the applied voltage, roughly 10 to 15 Angstroms per applied volt.

The etched and formed anode foils are cut and the capacitor assembled as discussed above. A multi-anode capacitor stack according to the present invention consists of a number of units of: cathode, a spacer, two or more anodes, a spacer and cathode; with neighboring units sharing the cathode between them.

Any spacer capable of holding the electrolyte is used in the present invention. Many examples of spacers for use are well known. Examples include, but are not limited to, paper or synthetic spacers. Specific examples include paper spacers wettable by BLO-based solvents. Kraft paper spacers would not be used, if they cannot be wetted by the electrolytes. Specific examples of synthetic spacers include poly(olefin) spacers, such as poly(ethylene) and poly(propylene) spacers, including, but not limited to, Celgard® spacers. Preferably, the spacer consists of one or more layers of appropriate manila, esparto, or hemp papers, which are low density and allow the electrolyte to wick through for contact from anode to cathode. Alternatively, the spacer could be one or more sheets of Celgard, a porous polypropylene, polyethylene, or blend which also allows electrolyte to wick through while still maintaining mechanical separation between the anode and cathode.

The electrolyte of the present invention is then prepared. While the various ingredients may be mixed in any order, one exemplary method involves mixing the γ-butyrolactone, alcohol and acid together, followed by the acetonitrile, the amine and other components. Other exemplary methods of preparing the electrolytes of the present invention are given below.

The pre-assembled capacitor is then vacuum impregnated with the electrolyte of the present invention, by placing the capacitor in contact with the electrolyte and reducing the pressure to less than 50 cm Hg. The capacitor is held at this low pressure for about 5 to 45 minutes. In one example, the capacitor is held for about 30 minutes, and then pressure is restored, using the pressure to force the electrolyte mixture into the capacitor stack. The capacitor is then removed and placed in a oven that is heated to about 65° C. to about 90° C. for a period of 2 to 24 hours. In one example, the capacitor is heated for about 4 hours. The capacitor is then aged in a normal manner by applying the working voltage to the capacitor, allowing the capacitor to reach this voltage, and then allowing the current to decrease.

Electrolytic capacitors according to the present invention can be incorporated into implantable medical devices, such as implantable cardioverter defibrillators (ICDs), as would be apparent to one skilled in the art, as described in U.S. Pat. No. 5,522,851 issued to Fayram.

In another embodiment, the present invention relates to an electrolytic capacitor impregnated with one or more of the conductive electrolytes of the present invention.

In another embodiment, the present invention relates to an implantable cardioverter defibrillator (ICD) comprising an electrolytic capacitor impregnated with one or more of the conductive electrolytes of the present invention.

The following examples are illustrative, but not limiting, of the method and compositions of the present invention. Other suitable modifications and adaptations of the variety of conditions and parameters encountered in electrolyte preparation and processing that would be known to those skilled in the art are within the spirit and scope of the invention.

EXAMPLES

The properties of the prepared electrolytes were measured in a atmosphere-controlled environment. Slide capacitor experiments were performed at 37° C., using a commercially available etched aluminum anode, a commercially available aluminum cathode and commercially available spacers. Glass slide dimensions are 1"×3". The following spacers are commercially available: ME4-type manila paper (Nippon Kodoshi Kogyo, Agawagun, Japan), MER-type manila and esparto paper (Nippon Kodoshi Kogyo, Agawagun, Japan), MR5D3-type manila and esparto duplex paper (Nippon Kodoshi Kogyo, Agawagun, Japan), WED-type manila and kraft duplex paper (Nippon Kodoshi Kogyo, Agawagun, Japan), WE3-type hemp paper (Nippon Kodoshi Kogyo, Agawagun, Japan), ND-type Kraft paper (MH Dielectrics, Inc., Mount Holly Springs, Pa.) and Celgard-type poly(olefin) separators (Celgard L. L. C., Charlotte, N.C.).

As is well known in the art, the breakdown voltage of an electrolyte can be used as a gauge to determine whether an electrolyte will perform well in very high voltage electrolytic capacitors. Methods for determining the breakdown voltage of electrolytes are well known in the art. An example of such methods include, but is not limited to open cup scintillation voltage.

The formulations in the following examples, unless otherwise stated, express component amounts in grams.

Example 1

An electrolyte was prepared having the following formulation:

| | |
|---|---|
| γ-Butyrolactone | 120.2 |
| Dodecanedioic acid | 10.0 |
| Glycerol | 6.0 |
| 4-Nitrobenzyl alcohol | 2.0 |
| Acetonitrile | 6.0 |
| Hypophosphorous acid | 0.5 |
| Triethylamine | 3.5 |

The γ-butyrolactone was placed in a 200 mL beaker and heated to about 60° C. The dodecanedioic acid was added and the solution temperature was raised to about 90° C. and heated at about 90-100° C. for about 1 hour. The nitrobenzyl alcohol was added, was allowed to dissolve, and the solution was removed from the hot plate. The solution was cooled to about room temperature and it turned into a gel. The triethylamine was added and the mixture formed a viscous solution.

Example 2

An electrolyte was prepared having the following formulation:

| | |
|---|---|
| Ethylene glycol | 61.2 |
| γ-Butyrolactone | 56.6 |
| 1,2-Propanediol | 33.3 |
| Acetonitrile | 4.5 |
| Azelaic acid | 9.0 |
| Boric acid | 1.6 |
| Water | 7.6 |
| Triethylamine | 8.2 |

The ethylene glycol, γ-butyrolactone and 1,2-propanediol were mixed in a 200 mL beaker and heated to about 70° C. The azelaic and boric acid was added and the solution was heated to about 110° C. and held at about 110-130° C. for about 1 hour. The solution was cooled to about 100° C., the nitroacetophenone was added, and the solution was cooled to about room temperature. The acetonitrile and water were added to the solution. The solution pH (23.6° C.) was about 3.04 and the conductivity was about 1.48 µS/cm. The triethylamine was added to the solution.

The resultant electrolyte exhibited a pH (37.8° C.) of 7.03 and a conductivity (37.3° C.) of 2.59 µS/cm. Water content was measured by an average Karl Fischer titration, and was determined to be 4.47%. The index of refraction (20° C.) was 1.4344. The average viscosity was 7.15 cP (36.5° C.) and the electrolyte had a density of 1.069 g/mL. An open cup scintillation voltage of 445 V was observed.

Slide capacitors composed of either a single or a double layer anode interleaved between four 0.25 mil Kraft paper spacers and a conventional cathode were impregnated with the prepared electrolyte. The single anode capacitor exhibited a capacitance of 3.3380 µF, an Equivalent Series Resistance (ESR) of 33.52Ω and a breakdown voltage of 325 V. When employed in a dual-anode layer capacitor arrangement, the capacitor obtained a capacitance of 7.8471 µF and an ESR of 28.95Ω.

Example 3

An electrolyte was prepared having the following formulation:

| | |
|---|---|
| γ-Butyrolactone | 131.7 |
| Glycerol | 7.5 |
| Dodecanedioic acid | 2.0 |
| 4-Nitrobenzyl alcohol | 0.8 |
| Disopropylethylamine | 0.9 |
| Acetonitrile | 7.4 |

The γ-butyrolactone and glycerol were mixed in a 200 mL tall form beaker and heated to about 80° C. The dodecanedioic acid and nitrobenzyl alcohol were added and the solution was allowed to cool. When the solution cooled to about 35° C., the acetonitrile and diisopropylethylamine were added.

The resultant electrolyte exhibited a pH (37.0° C.) of 7.92 and a conductivity (37.0° C.) of 637 µS/cm. Average Karl Fischer titration (water content) was 1.52%. The index of refraction (20° C.) was 1.4348. The average viscosity was 1.86 cP (37° C.) and the electrolyte had a density of 1.097 g/mL. An open cup scintillation voltage of 578 V was observed.

Slide capacitors composed of either a single or a double layer anode interleaved between various spacers and a conventional cathode were impregnated with the prepared electrolyte. For the 3-layer ND spacer, the single anode capacitor exhibited a capacitance of 1.195 µF, an ESR of 1.7587Ω and a breakdown voltage of greater than 750 V. For the Celgard® spacer, the single anode capacitor exhibited a capacitance of 3.1259 µF, an ESR of 15.33Ω and a breakdown voltage of 600 V. For the ME4 spacer, the single anode capacitor exhibited a capacitance of 2.4771 µF, an ESR of 42.96Ω and a breakdown voltage of 620 V. For the MER spacer, the single anode capacitor exhibited a capacitance of 2.5612 µF, an ESR of 46.22Ω and a breakdown voltage of 697 V. For the 2 layer MHx 2-40 spacer, the single anode capacitor exhibited a capacitance of 3.1928 µF, an ESR of 20.89Ω and a breakdown voltage of 533 V. For the 2 layer MHx 2.5-40 spacer, the single anode capacitor exhibited a capacitance of 3.0923 µF, an ESR of 27.64Ω and a breakdown voltage of 649 V. For the 2 layer MHK 2-40 paper spacer, the single anode capacitor exhibited a capacitance of 3.1079 µF, an ESR of 26.37Ω and a breakdown voltage of 608 V. For the 2 layer MH 2-40 paper spacer, the single anode capacitor exhibited a capacitance of 3.1516 µF, an ESR of 19.94Ω and a breakdown voltage of 589V. For the 2 layer MH 2.5-40 paper spacer, the single anode capacitor exhibited a capacitance of 3.0862 µF, an ESR of 31.24Ω and a breakdown voltage of 650 V.

When employed in a dual-anode layer capacitor arrangement, the capacitor exhibited the following values. For the 3 layer ND spacer, a capacitance of 932.8 nF and an ESR of 3.0959 kΩ was observed. For the Celgard® spacer, a capacitance of 2.6890 nF and an ESR of 265.2 kΩ was observed. For the ME4 spacer, a capacitance of 3.1110 µF and an ESR of 109.8Ω was observed. For the MER spacer, a capacitance of 1.5164 µF and an ESR of 561.5Ω was observed.

Example 4

An electrolyte was prepared having the following formulation:

| | |
|---|---|
| γ-Butyrolactone | 131.7 |
| Glycerol | 8.0 |
| 3-tert-Butyladipic acid | 1.8 |
| 4-Nitrobenzyl alcohol | 0.8 |
| Diisopropylethylamine | 1.0 |
| Acetonitrile | 7.4 |

The γ-butyrolactone and glycerol were heated to about 100° C. and the 3-tert-Butyladipic acid and 4-nitrobenzyl alcohol was added. The solution was then allowed to cool to about 40° C. The diisopropylethylamine and acetonitrile were added with mixing.

The resultant electrolyte exhibited a pH (36.8° C.) of 7.73 and a conductivity (36.4° C.) of 717 µS/cm. Average Karl Fischer titration (water content) was 0.07%. The index of refraction (20° C.) was 1.4349. The average viscosity was 1.91 cP (37° C.) and the electrolyte had a density of 1.101 g/mL. An open cup scintillation voltage of 586 V was observed.

Slide capacitors composed of either a single or a double layer anode interleaved between various spacers and a conventional cathode were impregnated with the prepared electrolyte. For the 3-layer ND spacer, the single anode capacitor exhibited a capacitance of 1.570 µF, an ESR of 923.4Ω, and a breakdown voltage greater than 750 Volts. For the single layer Celgard® spacer, the single anode capacitor exhibited a capacitance of 3.1171 µF, an ESR of 13.15Ω, and a breakdown voltage of 604 Volts. For the single layer WE3 spacer, the single anode capacitor exhibited a capacitance of 3.1202 µF, an ESR of 21.76Ω, and a breakdown voltage of 611 Volts. For the MR5D3 spacer, the single anode capacitor exhibited a capacitance of 3.0668 µF, ESR of 37.02Ω, and a breakdown voltage of 680 Volts.

When employed in a dual-anode layer capacitor arrangement, the capacitor exhibited the following values. For the 3-layer ND spacer, a capacitance of 1.9450 µF and an ESR of 1.481 kΩ was observed. For the single layer Celgard® spacer, a capacitance of 4.922 µF and an ESR of 97.20Ω was observed. For the WE3 spacer a capacitance of 3.5211 µF and an ESR of 112.3Ω was observed. For the MR5D3 spacer a capacitance of 3.6969 µF and an ESR of 93.50Ω was observed.

Example 5

An electrolyte was prepared having the following formulation:

| | |
|---|---|
| γ-Butyrolactone | 131.7 |
| Glycerol | 7.4 |
| Adipic acid | 5.0 |
| 4-Nitrobenzyl alcohol | 0.8 |
| Acetonitrile | 7.4 |
| Triethylamine | 3.6 |

The γ-butyrolactone and glycerol were mixed in a 200 mL tall form beaker and heated to about 60° C. The adipic acid and 4-nitrobenzyl alcohol was added and the mixture was heated to about 75° C. to allow for complete dissolution. The solution was then removed from heating and allowed to cool. When the solution reached about 30° C., the acetonitrile and triethylamine were added.

The resultant electrolyte exhibited a pH (39.0° C.) of 7.59 and conductivity (38.6° C.) of 935 µS/cm. Average Karl Fischer titration (water content) was 0.14%. The index of refraction (20° C.) was 1.4370. The average viscosity was 2.27 cP (37° C.) and the electrolyte had a density of 1.098 g/mL. An open cup scintillation voltage of 445 V was observed.

Slide capacitors composed of either a single or a double layer anode interleaved between various spacers and a conventional cathode were impregnated with the prepared electrolyte. For the 3-layer ND spacer, the single anode capacitor exhibited a capacitance of 2.2584 µF, an ESR of 174.4Ω, and a breakdown voltage greater than 542 Volts. For the single layer Celgard® spacer, the single anode capacitor exhibited a capacitance of 3.0762 µF, an ESR of 15.73Ω, and a breakdown voltage of 476 Volts. For the single layer WE3 spacer, the single anode capacitor exhibited a capacitance of 3.1009 µF, an ESR of 21.4Ω, and a breakdown voltage of 475 Volts. For the MR5D3 spacer, the single anode capacitor exhibited a capacitance of 3.2700 µF, an ESR of 25.08Ω, and a breakdown voltage of 477 Volts.

When employed in a dual-anode layer capacitor arrangement, the capacitor exhibited the following values. For the 3-layer ND spacer, a capacitance of 2.2929 µF and an ESR of 450.3Ω was observed. For the single layer Celgard® spacer, a capacitance of 4.6422 µF and an ESR of 99.70Ω was observed. For the WE3 spacer a capacitance of 3.6400 µF and an ESR of 64.26Ω was observed. For the MR5D3 spacer a capacitance of 4.3346 µF and an ESR of 100.9Ω was observed.

Example 6

An electrolyte was prepared having the following formulation:

| | |
|---|---|
| γ-Butyrolactone | 111.9 |
| Glycerol | 7.6 |
| Diethylene glycol butyl ether | 37.2 |
| Dodecanedioic acid | 2.0 |
| 4-Nitrobenzyl alcohol | 0.8 |
| Hypophosphorous acid | 0.2 |
| Acetonitrile | 7.5 |
| Diisopropylethylamine | 1.1 |

The γ-butyrolactone, glycerol, diethylene glycol butyl ether and hypophosphorous acid were placed in a 200 mL tall form beaker and the mixture was heated to about 40° C. Dodecanedioic acid and 4-nitrobenzyl alcohol were added and the mixture was heated until it was clear (about 65° C.). The solution was cooled to about 40° C. and the acetonitrile and diisopropylethylamine were added.

The resultant electrolyte exhibited a pH (34.80° C.) of 7.64 and conductivity (35.3° C.) of 412 µS/cm. Average Karl Fischer titration (water content) was 0.23%. The index of refraction (20° C.) was 1.4349. The average viscosity was 2.422 cP (37° C.) and the electrolyte had a density of 1.055 g/mL. An open cup scintillation voltage of 510 V was observed.

Slide capacitors composed of either a single or a double layer anode interleaved between various spacers and a conventional cathode were impregnated with the prepared electrolyte. For the 3-layer ND spacer, the single anode capacitor exhibited a capacitance of 1.356 µF, an ESR of 1.1536 kΩ, and a breakdown voltage greater than 750 Volts. For the single layer Celgard® spacer, the single anode capacitor exhibited a capacitance of 3.0884 µF, an ESR of 15.16Ω, and a breakdown voltage of 570 Volts. For the single layer WE3 spacer, the single anode capacitor exhibited a capacitance of 3.0512 µF, an ESR of 22.04Ω, and a breakdown voltage of 593 Volts. For the MR5D3 spacer, the single anode capacitor exhibited a capacitance of 3.0976 µF, an ESR of 34.05Ω, and a breakdown voltage of 715 Volts. For the MHX 2-40 spacer, the single anode capacitor exhibited a capacitance of 3.1248 µF, an ESR of 21.62Ω, and a breakdown voltage of 633 Volts. For the MHK 2-40 spacer, the single anode capacitor exhibited a capacitance of 3.0515 µF, an ESR of 40.39Ω, and a breakdown voltage of 610 Volts.

When employed in a dual-anode layer capacitor arrangement, the capacitor exhibited the following values. For the 3-layer ND spacer, a capacitance of 843.2 nF and an ESR of 3.2665 kΩ was observed. For the single layer Celgard® spacer, a capacitance of 3.6808 µF and an ESR of 99.28Ω was observed. For the WE3 spacer a capacitance of 3.5658 µF and an ESR of 100.8Ω was observed. For the MR5D3 spacer a capacitance of 3.3324 µF and an ESR of 100.4Ω was observed.

Example 7

An electrolyte was prepared having the following formulation:

| | |
|---|---|
| γ-Butyrolactone | 87.8 |
| 1-Methyl-2-pyrrolidinone (NMP) | 50.5 |
| Glycerol | 7.4 |
| Dodecanedioic acid | 2.0 |
| 4-Nitrobenzyl alcohol | 0.8 |
| Diisopropylethylamine | 0.9 |
| Acetonitrile | 7.4 |

The γ-butyrolactone, NMP and glycerol were mixed in a 200 mL tall form beaker and heated to about 80° C. The dodecanedioic acid and 4-nitrobenzyl alcohol were added and allowed to dissolve. The solution was cooled to below 35° C. and the remaining components were added with thorough mixing.

The resultant electrolyte exhibited a pH (36.5° C.) of 8.50 and conductivity (36.5° C.) of 244 µS/cm. Average Karl Fischer titration (water content) was 0.15%. The index of refraction (20° C.) was 1.4471. The average viscosity was 1.78 cP (37° C.) and the electrolyte had a density of 1.075 g/mL. An open cup scintillation voltage of 655 V was observed.

Slide capacitors composed of either a single or a double layer anode interleaved between various spacers and a conventional cathode were impregnated with the prepared electrolyte. For the 3-layer ND spacer, the single anode capacitor exhibited a capacitance of 2.4836 µF, an ESR of 157.1Ω, and a breakdown voltage greater than 750 Volts. For the single layer Celgard® spacer, the single anode capacitor exhibited a capacitance of 2.9649 µF, an ESR of 99.90Ω, and a breakdown voltage of 650 Volts. For the MR5D3 spacer, the single anode capacitor exhibited a capacitance of 3.0392 µF, an ESR of 33.12 D, and a breakdown voltage greater than 750 Volts. For the single layer WE3 spacer, the single anode capacitor exhibited a capacitance of 3.1247 µF, an ESR of 22.45Ω, and a breakdown voltage of 587 Volts.

When employed in a dual-anode layer capacitor arrangement, the capacitor exhibited the following values. For the 3-layer ND spacer, a capacitance of 2.3612 µF and an ESR of 208.5Ω was observed. For the single layer Celgard® spacer, a capacitance of 3.1569 µF and an ESR of 61.00Ω was observed. For the MR5D3 spacer a capacitance of 3.4763 µF and an ESR of 75.85Ω was observed. For the WE3 spacer a capacitance of 3.1614 µF and an ESR of 71.05Ω was observed.

Example 8

An electrolyte was prepared having the following formulation:

| | |
|---|---|
| 1-Methyl-2-pyroldione (NMP) | 101.1 |
| γ-butyrolactone | 43.9 |
| Glycerol | 7.4 |
| Dodecanedioic acid | 2.0 |
| 4-Nitrobenzyl alcohol | 0.8 |
| Diisopropylethylamine | 0.9 |
| Acetonitrile | 7.4 |

The NMP, γ-butyrolactone, and glycerol were mixed in a 200 mL tall form beaker. The mixture was heated to about 80° C., the dodecanedioic acid and 4-nitrobenzyl alcohol were added and the solution was cooled to below about 35° C. The diisopropylethylamine and acetonitrile were added with thorough mixing.

The resultant electrolyte exhibited a pH (37.4° C.) of 9.27 and conductivity (37.7° C.) of 112 µS/cm. Average Karl Fischer titration (water content) was 0.18%. The index of refraction (20° C.) was 1.4583. The average viscosity was 1.68 cP (37° C.) and the electrolyte had a density of 1.048 g/mL. An open cup scintillation voltage of 700 V was observed.

Slide capacitors composed of either a single or a double layer anode interleaved between various spacers and a conventional cathode were impregnated with the prepared electrolyte. For the 3-layer ND spacer, the single anode capacitor exhibited a capacitance of 3.1743 µF, an ESR of 44.10Ω, and a breakdown voltage of 705 Volts. For the single layer Celgard® spacer, the single anode capacitor exhibited a capacitance of 3.1391 µF, an ESR of 18.22Ω, and a breakdown voltage of 630 Volts. For the MR5D3 spacer, the single anode capacitor exhibited a capacitance of 3.0636 µF, an ESR of 51.35Ω, and a breakdown voltage of 681 Volts. For the single layer WE3 spacer, the single anode capacitor exhibited a capacitance of 2.6667 µF, an ESR of 135.2Ω, and a breakdown voltage of 450 Volts.

When employed in a dual-anode layer capacitor arrangement, the capacitor exhibited the following values. For the 3-layer ND spacer, a capacitance of 2.3916 µF and an ESR of 83.53Ω was observed. For the single layer Celgard® spacer, a capacitance of 3.1387 µF and an ESR of 69.07Ω was observed. For the MR5D3 spacer a capacitance of 3.2645 µF and an ESR of 85.92Ω was observed. For the WE3 spacer a capacitance of 2.9278 µF and an ESR of 92.62Ω was observed.

Example 9

An electrolyte was prepared having the following formulation:

| | |
|---|---|
| γ-Butyrolactone | 131.4 |
| Glycerol | 7.5 |
| Dodecanedioic acid | 2.0 |
| 4-Nitrobenzyl alcohol | 0.8 |
| Triethylamine | 0.9 |
| Acetonitrile | 7.5 |

The γ-butyrolactone and glycerol were mixed in a 200 mL tall form beaker. The mixture was heated to about 55° C. and the dodecanedioic acid and 4-nitrobenzyl alcohol was added. The solution was heated to about 65° C., at which point all solids dissolved completely. The solution was allowed to partially cool. The triethylamine and acetonitrile were added with stirring.

The resultant electrolyte exhibited a pH (37.7° C.) of 8.36 and conductivity (37.8° C.) of 548 µS/cm. Average Karl Fischer titration (water content) was 0.33%. The average viscosity was 1.90 cP (37° C.) and the electrolyte had a density of 1.0926 g/mL. An open cup scintillation voltage of 583 V was observed.

Slide capacitors composed of either a single or a double layer anode interleaved between various spacers and a conventional cathode were impregnated with the prepared electrolyte. For the single layer Celgard® spacer, the single anode capacitor exhibited a capacitance of 3.0863 µF, an ESR of 18.11Ω, and a breakdown voltage of 595 Volts. For the MR5D3 spacer, the single anode capacitor exhibited a capacitance of 3.2323 µF, an ESR of 28.82Ω, and a breakdown voltage of 576 Volts. For the single layer WE3 spacer, the single anode capacitor exhibited a capacitance of 3.1880 µF, an ESR of 20.7Ω, and a breakdown voltage of 575 Volts.

When employed in a dual-anode layer capacitor arrangement, the capacitor exhibited the following values. For the single layer Celgard® spacer, a capacitance of 3.5008 µF and an ESR of 82.51Ω was observed. For the MR5D3 spacer a capacitance of 2.6477 µF and an ESR of 96.84Ω was observed. For the WE3 spacer a capacitance of 2.8671 µF and an ESR of 126.70Ω was observed.

Example 10

An electrolyte was prepared having the following formulation:

| | |
|---|---|
| γ-Butyrolactone | 131.5 |
| Ethylene glycol | 15.0 |
| Dodecanedioic acid (DDA) | 2.0 |
| 4-Nitrobenzyl alcohol | 0.9 |
| Triethylamine | 0.9 |

The γ-butyrolactone and ethylene glycol were mixed in a 200 mL tall form beaker. The mixture was heated to about 50° C. and the dodecanedioic acid and 4-nitrobenzyl alcohol were added. The solution was heated to about 65° C., at which point all solids dissolved. The solution was allowed to cool to about 40° C., and the triethylamine was added with stirring.

The resultant electrolyte exhibited a pH (37.5° C.) of 8.22 and conductivity (37.6° C.) of 665 µS/cm. Average Karl Fischer titration (water content) was 0.52%. The average viscosity was 2.13 cP (37° C.) and the electrolyte had a density of 1.098 g/mL. An open cup scintillation voltage of 560 V was observed.

Slide capacitors composed of either a single or a double layer anode interleaved between various spacers and a conventional cathode were impregnated with the prepared electrolyte. For the single layer Cegard® spacer, the single anode capacitor exhibited a capacitance of 3.3680 µF, an ESR of 21.15Ω, and a breakdown voltage of 588 Volts. For the MR5D3 spacer, the single anode capacitor exhibited a capacitance of 3.1985 µF, an ESR of 29.57Ω, and a breakdown voltage of 579 Volts. For the single layer WE3 spacer, the single anode capacitor exhibited a capacitance of 3.2009 µF, an ESR of 19.91Ω, and a breakdown voltage of 570 Volts.

When employed in a dual-anode layer capacitor arrangement, the capacitor exhibited the following values. For the single layer Celgard® spacer, a capacitance of 3.6830 µF and an ESR of 86.15Ω was observed. For the MR5D3 spacer a capacitance of 3.7100 µF and an ESR of 95.48Ω was observed. For the WE3 spacer a capacitance of 2.8102 µF and an ESR of 120.2Ω was observed.

Example 11

An electrolyte was prepared having the following formulation:

| | |
|---|---|
| γ-Butyrolactone | 131.4 |
| Glycerol | 15.0 |
| Dodecanedioic acid (DDA) | 2.0 |
| 4-Nitrobenzyl alcohol | 0.8 |
| Triethylamine | 0.9 |

The γ-butyrolactone and glycerol were mixed in a 200 mL tall form beaker and heated to about 45° C. The dodecanedioic acid and 4-nitrobenzyl alcohol were added and allowed to dissolve, while the temperature was raised to about 65° C. The solution was cooled to about 40° C. and the triethylamine and was added. The electrolyte pH (37.1° C.) was about 7.83 and the conductivity was about 656 µS/cm.

Example 12

An electrolyte was prepared having the following formulation:

| | |
|---|---|
| γ-Butyrolactone | 131.4 |
| 2-Methoxyethanol | 15.1 |
| Dodecanedioic acid (DDA) | 2.0 |
| 4-Nitrobenzyl alcohol | 0.8 |
| Triethylamine | 0.9 |

The γ-butyrolactone and the 2-methoxyethanol were mixed and heated to about 45° C. in a 200 mL tall form beaker. The dodecanedioic acid and 4-nitrobenzyl alcohol were added and allowed to dissolve as the mixture was heated to about 65° C. The solution was then allowed to cool to about 35° C. and the triethylamine was added. The electrolyte pH (32.1° C.) was about 7.90 and the conductivity was about 235 µS/cm.

Example 13

An electrolyte was prepared having the following formulation, component amounts are expressed in weight percent:

| | |
|---|---|
| γ-butyrolactone | 86.1 |
| Acetonitrile | 4.8 |
| Glycerin | 4.8 |
| Diisopropylethylamine | 1.3 |
| Dodecanedioic acid | 2.6 |
| 3-Nitrobenzyl alcohol | 0.5 |

Weights were calculated to produce two liters of material. First, the solvents were mixed in the order presented. Glycerin was difficult to mix thoroughly in this system, so mixing was carried out at about 80° C. for at least one hour. One half of the dodecanedioic acid was added slowly to prevent clumping. The particles of dodecanedioic acid remained suspended in the solution until one half of the diisopropylethylamine was added. The mixture was stirred at about 80° C. for about 30 minutes, until only a clear, non stratified liquid remained.

The pH and conductivity were tested to determine the exact amount of diisopropylethylamine required to bring the pH in the range of 5.5 to 7. Also, because dodecanedioic acid was not added in exactly stoichiometric amount, compared to the diisopropylethylamine, the pH was monitored. The second adjusted half of dodecanedioic acid and diisopropylethylamine was added with stirring over an additional 30 minutes. The 3-nitrobenzyl alcohol was added and the solution was allowed to cool to 25° C.

The resultant electrolyte exhibited a pH of about 7 by litmus paper. The conductivity was 1.98 mS/cm at 25° C. and 3.09 mS/cm at 75° C. The viscosity was measured as 29 seconds in a Zahn cup. The index of refraction was 1.430 at 25° C. An open cup scintillation breakdown voltage of 573 V was observed.

Example 14

An electrolyte of the following composition was prepared for testing with large electrolytic capacitors. Component amounts are expressed in weight percent.

| | |
|---|---|
| γ-butyrolactone | 87.8 |
| Acetonitrile | 4.9 |
| Glycerin | 4.9 |
| Diisopropylethylamine | 0.6 |
| Dodecanedioic acid | 1.3 |
| 3-Nitrobenzyl alcohol | 0.5 |

Weights were calculated to produce about one liter of material. Preparation followed that of Example 13.

Figure 2:
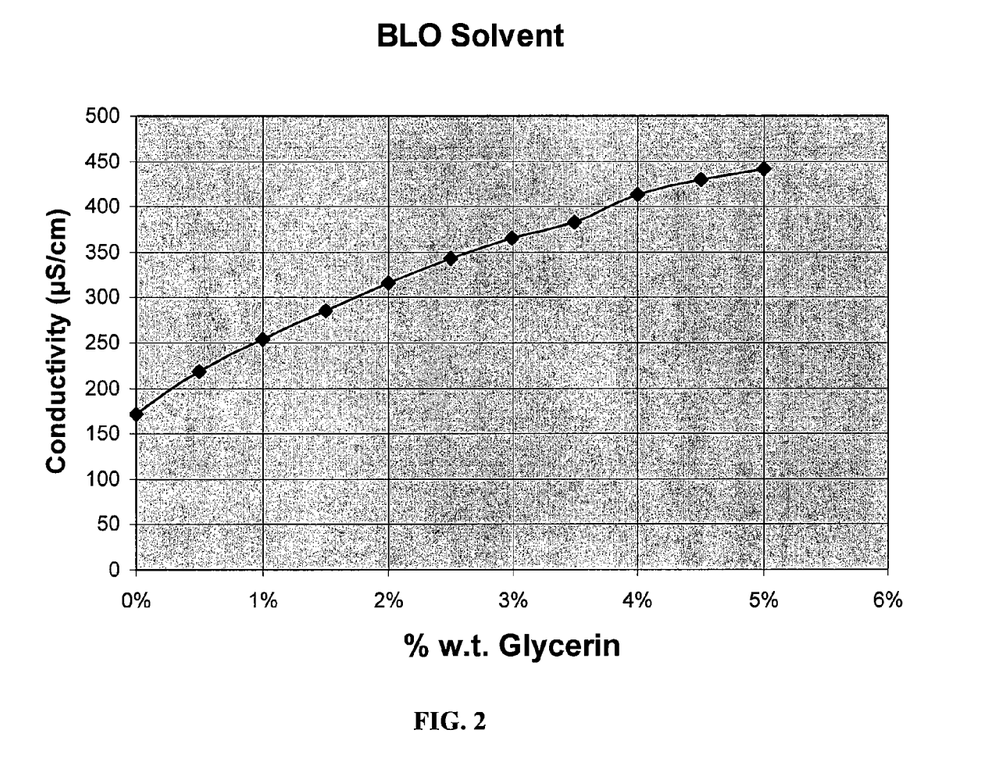
FIG. 2 is a graphical representation of the dependence of conductivity on amount of glycerin, in the electrolyte of Example 14.

As shown in FIG. 2, the conductivity of this γ-butyrolactone-based electrolyte increased with increasing concentration of glycerin. The electrolyte in FIG. 2 is formulated with the conducting species shown in this example, but contains no acetonitrile.

The resultant electrolyte exhibited a pH of about 7 by litmus paper. The conductivity was 0.5 mS/cm at 25° C. The viscosity was measured as 30 seconds in a Zahn cup. The index of refraction was 1.430 at 25° C. An open cup scintillation breakdown voltage of 620 V was observed.

Large electrolytic capacitors were constructed for the purpose of testing this electrolyte in completed units. Highly etched aluminum foil was prepared with an aluminum oxide coating of sufficient thickness to withstand more than 800 volts in an electrolytic bath of suitable ionic conductors. Medium density electronic grade papers were chosen from a group known for ease of swelling in the presence of γ-butyrolactone. Along with aluminum cathode material, these were formed in a 'jelly roll' fashion such that the anode and cathode material were separated by the paper material.

This system was heated and dried in a vacuum oven with vacuum of more than 28 inches of mercury and temperatures between 70° C. and 95° C. for about 10 minutes to about 30 minutes before impregnation of the electrolyte. Positive pressure of about 50 p.s.i. to about 65 p.s.i. was applied for about an additional 20 minutes. Control units using a commercially available electrolyte were treated in the same fashion.

Units were allowed to cool in a controlled environment to exclude any moisture from being re-introduced to the units. The rolls were placed in containment enclosures with external electrical connections to the anode and cathode aluminum foils.

The anode foil was connected to the positive terminal of an appropriate power supply. At about room temperature the cathode was attached to the negative terminal and voltage was applied through a system that limited the current passing through the capacitor. The voltage was allowed to rise to about 620 Volts over a period of several hours. The voltage was lowered to about 610 Volts and the unit was externally heated to about 85° C. The units remained in this condition until the current had dropped to a predetermined low level. Units were removed from the power supply and allowed to cool to 25° C. for measurements.

Units made with the electrolyte of this invention were compared to those made with commercially available electrolyte. The commercial electrolyte had a conductivity of about 0.45 mS/cm$^2$ higher than that of the present example.

Figure 3:
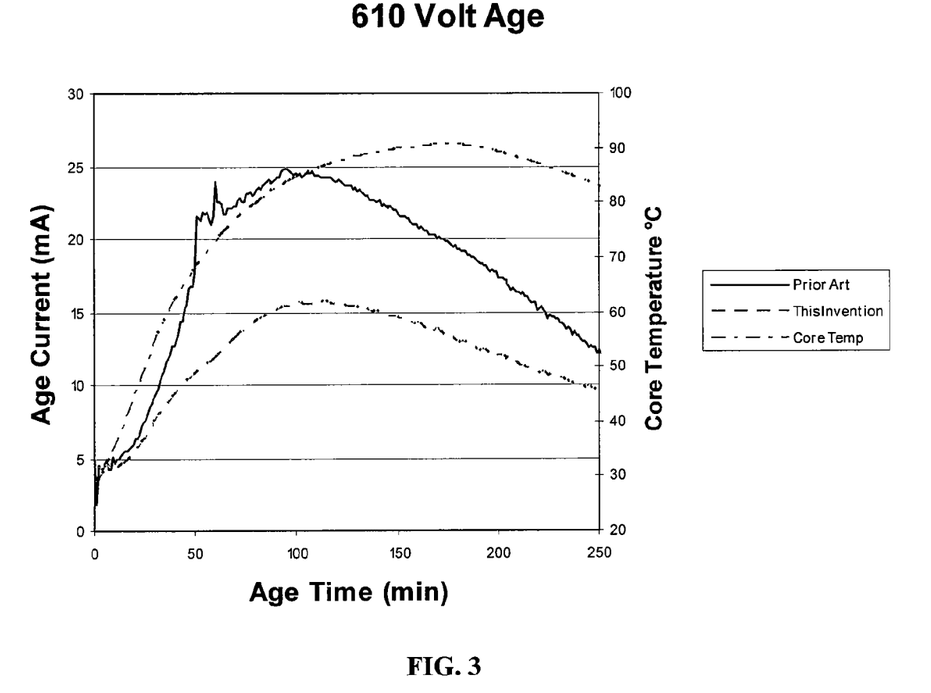
FIG. 3 is a graphical representation of the increase in the number and severity of minute breakdowns occurring in large electrolytic capacitors containing an electrolyte of the present invention vs. a commercial electrolyte.

As shown in FIG. 3, an increase in the number and severity of minute break downs occurs in large electrolytic capacitors at 610 Volts as the units were heated to 85 C. Both units had been aged previously to 620 volts at 25° C. The current spikes of the units made with commercial electrolyte is compared with that of the present example showing lower levels of current spikes. These spikes also occur during the normal lifetime of the device. Reducing the number of breakdowns and lowering the energy dissipated during these current excursions increases the short and long term reliability of capacitors made with the electrolyte of this invention.

Electrical measurements made on units using the electrolyte of this example and units made with commercial electrolyte are summarized in the table below.

| Electrolyte | Cap. μF | % D |
|---|---|---|
| Commercial | 1995 | 0.030 |
| Example 14 | 1877 | 0.042 |

A shorter length of capacitor anode foil was used in the units containing the electrolyte formulated in this example, which resulted in an artificially lower capacitance value. The realization of capacitance is about equal to the units containing the commercial electrolyte. The difference in ESR (% D) is attributed to the paper swelling factor which is lower for the units containing the formulated in this example.

Example 15

An electrolyte of the following composition was prepared for testing preliminary electrolyte parameters. Component amounts are expressed in weight percent.

| | |
|---|---|
| γ-butyrolactone | 89.1 |
| Acetonitrile | 5.0 |
| Glycerin | 5.0 |
| Triethylamine | 0.5 |
| Dodecanedioic acid | 1.3 |
| 3-Nitrobenzyl alcohol | 1.0 |

Weights were calculated such that 1 liter of electrolyte was prepared. The electrolyte was prepared according to the procedure of Example 13. Triethylamine was used in place of diisopropylethylamine with the result that the solution remained cloudy with suspended dodecanedioic acid until sufficient extra triethylamine was added to dissolve it (approximately 2 grams was added). Commensurate variations of pH and conductivity were seen. Results are shown in the table below.

| Variation of Example 15 | pH | Conductivity (mS/cm) |
|---|---|---|
| No variation | 7.48 | 0.37 |
| Additional 1 g TEA | 7.61 | 0.44 |
| Additional 2 g TEA | 7.72 | 0.55 |
| Additional 3 g TEA | 8.1 | 0.62 |

The open cell scintillation voltage was about 590 volts.

It is clear from above that the electrolyte conductivity can be controlled by adjusting the electrolyte pH through either additions of acid or amine.

Example 16

An electrolyte of the following composition was prepared for testing with relatively smaller electrolytic capacitors.

| | |
|---|---|
| γ-butyrolactone | 87.8 |
| Acetonitrile | 4.9 |
| Glycerin | 4.9 |
| Diisopropylethylamine (DIPEA) | 0.6 |
| Dodecanedioic acid | 1.3 |
| 3-Nitrobenzyl alcohol | 0.5 |

Weights were calculated such that 1 liter of electrolyte was prepared The electrolyte was prepared according to the procedure of Example 13. Several variations of this example were prepared and the results are shown below.

| Variation on Example 16 | pH | Conductivity (mS/cm) |
|---|---|---|
| No variation | 7.48 | 0.46 |
| Additional 5 g DIPEA | 7.61 | 0.68 |
| Additional 5 g DIPEA + 10 g H$_2$O | 7.72 | 0.70 |
| Additional 5 g DIPEA + 20 g H$_2$O | 7.72 | 0.72 |

Open cell scintillation voltage for the electrolyte of this example (no variation) measured 610 volts. Electrolytic capacitors were constructed similar to the description presented in Example 14. These units were smaller than those of this example, having a capacity of 180 μF, with a rate voltage of 600 WV.

Figure 4:
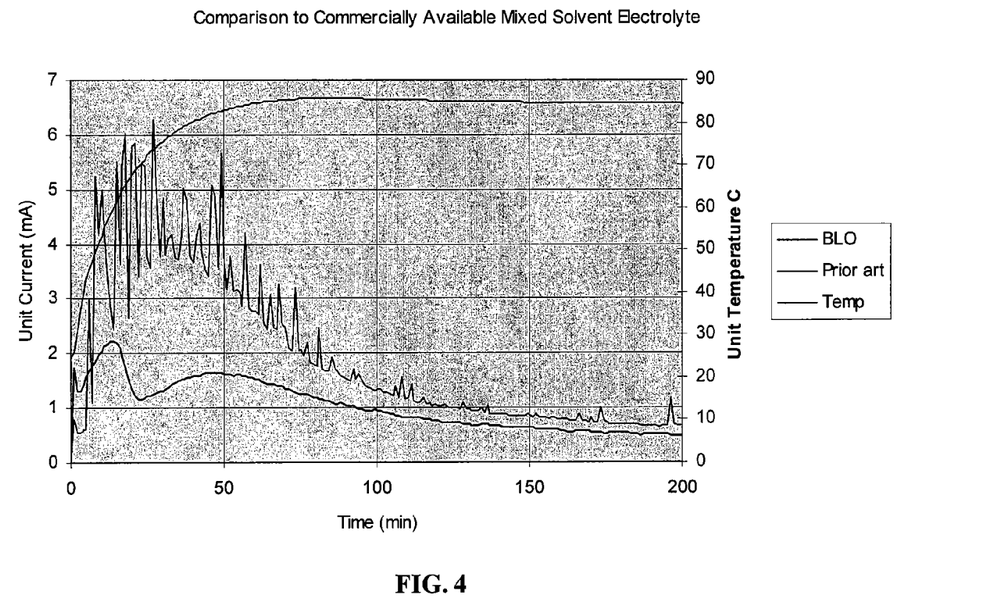
FIG. 4 is a graphical representation of the increase in the number and severity of minute breakdowns occurring in small electrolytic capacitor containing an electrolyte of the present invention vs. a commercial electrolyte.

As shown in FIG. 4, minute breakdowns occur during the extension of the aging process to 85° C. The electrolyte formulated in this example has fewer breakdowns than the commercial electrolyte. This demonstrates that electrolytes of the present invention result in more highly reliable capacitors compared to those prepared with the commercially available electrolyte.

| Unit # | Cap. μF | ESR (mΩ) |
|---|---|---|
| 1 | 182 | 0.568 |
| 2 | 184 | 0.473 |
| 3 | 183 | 0.506 |
| 4 | 182 | 0.510 |
| Commercial Electrolyte | 183 | 0.411 |

Although somewhat higher in resistance, no corrosion was detected in the units made with the electrolyte of this example. Also, the higher reliability represented by the high temperature breakdown and repair mechanisms of the capacitors containing electrolytes of the present invention is very important in many applications.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

The invention claimed is:

1. A conductive electrolyte for an electrolytic capacitor, comprising:
   γ-butyrolactone;
   acetonitrile; and
   glycerol,
   wherein the electrolyte is about 75 wt % to about 95 wt % γ-butyrolactone.

2. The electrolyte of claim 1, comprising about 1 wt % to about 10 wt % acetonitrile.

3. The electrolyte of claim 1, comprising about 1 wt % to about 10 wt % glycerol.

4. The electrolyte of claim 1, further comprising:
   an ionic salt resulting from the combination of an amine and a dicarboxylic acid.

5. The electrolyte of claim 4, wherein said amine is selected from the group consisting of ammonia, methyl amine, dimethylamine, trimethylamine, ethylamine, diethylamine, triethylamine, ethanolamine, diethanolamine, triethanolamine and diisopropylethylamine.

6. The electrolyte of claim 4, wherein said dicarboxylic acid is an aliphatic dicarboxylic acid of carbon chain length from five to fifteen ($C_5$-$C_{15}$).

7. The electrolyte of claim 1, further comprising a cathode depolarizer selected from the group consisting of nitrobenzene, nitrotoluene, nitrophenol, nitroacetophenone, nitrobenzyl alcohol and nitroanisole.

8. The electrolyte of claim 1, further comprising hypophosphorous acid.

9. An electrolytic capacitor having a working voltage greater than about 500 Volts and impregnated with a conductive electrolyte comprising:
   γ-butyrolactone;
   acetonitrile; and
   glycerol.

10. The electrolytic capacitor of claim 9 wherein said working voltage is in the range of greater than about 500 to about 750 Volts.

11. An implantable cardioverter defibrillator (ICD) comprising the electrolytic capacitor of claim 9.

12. A conductive electrolyte for an electrolytic capacitor, comprising:
about 45 wt % to about 85 wt % γ-butyrolactone;
about 5 wt % to about 45 wt % N-methylpyrrolidinone;
about 1 wt % to about 10 wt % acetonitrile; and
about 1 wt % to about 10 wt % of an alcohol, wherein the alcohol is selected from the group consisting of glycerol, diethylene glycol monoalkyl ether, 2-alkoxy ethanol and mixtures thereof.

13. The electrolyte of claim 12, wherein the alcohol is a diethylene glycol monoalkyl ether selected from the group consisting of diethylene glycol monomethyl ether, diethylene glycol monoethyl ether, diethylene glycol monopropyl ether, diethylene glycol monobutyl ether, diethylene glycol monopentyl ether and diethylene glycol monohexyl ether.

14. The electrolyte of claim 12, wherein the alcohol is a 2-alkoxy ethanol and said 2-alkoxy ethanol is selected from the group consisting of 2-methoxy ethanol, 2-ethoxy ethanol, 2-propoxy ethanol, 2-butoxy ethanol, 2-pentoxy ethanol, 2-hexyloxy ethanol, 2-heptyloxy ethanol and 2-octyloxy ethanol.

15. A conductive electrolyte for an electrolytic capacitor, comprising:
about 75 wt % to about 95 wt % γ-butyrolactone;
about 1 wt % to about 10 wt % DMSO; and
about 1 wt % to about 10 wt % of an alcohol, wherein the alcohol is selected from the group consisting of glycerol, diethylene glycol monoalkyl ether, 2-alkoxy ethanol and mixtures thereof.

16. The electrolyte of claim 15, wherein the alcohol is a diethylene glycol monoalkyl ether selected from the group consisting of diethylene glycol monomethyl ether, diethylene glycol monoethyl ether, diethylene glycol monopropyl ether, diethylene glycol monobutyl ether, diethylene glycol monopentyl ether and diethylene glycol monohexyl ether.

17. The electrolyte of claim 15, wherein the alcohol is a 2-alkoxy ethanol selected from the group consisting of 2-methoxy ethanol, 2-ethoxy ethanol, 2-propoxy ethanol, 2-butoxy ethanol, 2-pentoxy ethanol, 2-hexyloxy ethanol, 2-heptyloxy ethanol and 2-octyloxy ethanol.

18. A conductive electrolyte for an electrolytic capacitor, comprising:
γ-butyrolactone;
acetonitrile;
glycerol;
dodecanedioic acid;
diisopropylethylamine; and
3-nitrobenzyl alcohol.

19. The electrolyte of claim 18 comprising:
about 80 wt % to about 90 wt % γ-butyrolactone;
about 4 wt % to about 6 wt % acetonitrile;
about 4 wt % to about 6 wt % glycerol;
not more than about 10 wt % dodecanedioic acid;
not more than about 5.0 wt % diisopropylethylamine; and
not more than about 3.0 wt % 3-nitrobenzyl alcohol.

* * * * *